(12) United States Patent
Jia et al.

(10) Patent No.: US 11,929,159 B2
(45) Date of Patent: Mar. 12, 2024

(54) METHODS OF DETERMINING INSULIN INJECTION AMOUNT, COMPUTER STORAGE MEDIUMS AND DEVICES

(71) Applicants: SHANGHAI SIXTH PEOPLE'S HOSPITAL, Shanghai (CN); SHANGHAI JIAO TONG UNIVERSITY, Shanghai (CN)

(72) Inventors: Weiping Jia, Shanghai (CN); Bin Sheng, Shanghai (CN); Jian Zhou, Shanghai (CN); Ruhan Liu, Shanghai (CN); Liang Wu, Shanghai (CN); Huating Li, Shanghai (CN)

(73) Assignees: SHANGHAI SIXTH PEOPLE'S HOSPITAL, Shanghai (CN); SHANGHAI JIAO TONG UNIVERSITY, Shanghai (CN)

( * ) Notice: Subject to any disclaimer, the term of this patent is extended or adjusted under 35 U.S.C. 154(b) by 1196 days.

(21) Appl. No.: 16/470,798

(22) PCT Filed: Nov. 23, 2018

(86) PCT No.: PCT/CN2018/117211
§ 371 (c)(1),
(2) Date: Jun. 18, 2019

(87) PCT Pub. No.: WO2020/087602
PCT Pub. Date: May 7, 2020

(65) Prior Publication Data
US 2021/0383911 A1    Dec. 9, 2021

(30) Foreign Application Priority Data
Nov. 1, 2018    (CN) .......................... 201811295492.6

(51) Int. Cl.
*G16H 20/17*    (2018.01)
*A61M 5/142*    (2006.01)
(Continued)

(52) U.S. Cl.
CPC ............ *G16H 20/17* (2018.01); *A61M 5/142* (2013.01); *A61M 2005/14208* (2013.01);
(Continued)

(58) Field of Classification Search
CPC ........ G16H 20/17; G16H 40/67; G16H 50/20; A61M 5/142; A61M 2005/14208;
(Continued)

(56) References Cited

U.S. PATENT DOCUMENTS

2006/0015263 A1* 1/2006 Stupp ...................... G06F 17/18
702/19
2008/0306353 A1* 12/2008 Douglas ................. G16H 40/63
600/301
(Continued)

FOREIGN PATENT DOCUMENTS

WO    WO-2015166489 A2 * 11/2015 ......... G06F 19/3475

*Primary Examiner* — Neal Sereboff
(74) *Attorney, Agent, or Firm* — Dorsey & Whitney LLP (57) ABSTRACT

Method of determining insulin injection amount, computer storage medium, and devices, the method includes including: obtaining characteristic information and a blood glucose content at a current time of a target user; and determining an insulin injection amount at each time of the target user based on the characteristic information of the target user, the blood glucose content at the current time of the target user, a predetermined blood glucose prediction model, and a predetermined insulin injection amount prediction model. The method can facilitate the determination of the insulin injection amount at each time.

4 Claims, 6 Drawing Sheets

--- the characteristic information and the blood glucose content at a current time of a target user are obtained — S110 the insulin injection amount at each time of the target user is determined based on the characteristic information of the target user, the blood glucose content at the current time of the target user, the predetermined blood glucose prediction model, and the predetermined insulin injection amount prediction model — S120

(51) Int. Cl.
   *G06N 3/08* (2023.01)
   *G06N 20/00* (2019.01)
(52) U.S. Cl.
   CPC ......... *A61M 2230/201* (2013.01); *G06N 3/08* (2013.01); *G06N 20/00* (2019.01)
(58) Field of Classification Search
   CPC ........ A61M 2230/201; A61M 5/14244; G06N 3/08; G06N 20/00; G06Q 50/20–26
   See application file for complete search history.

(56) References Cited

U.S. PATENT DOCUMENTS

| | | | |
|---|---|---|---|
| 2010/0209506 A1* | 8/2010 | Eisenreich | A61P 9/00 514/263.21 |
| 2017/0106009 A1* | 4/2017 | Mayoux | A61P 43/00 |
| 2017/0220751 A1* | 8/2017 | Davis | G06N 5/048 |
| 2018/0353698 A1* | 12/2018 | Saint | A61M 5/31546 |
| 2019/0252079 A1* | 8/2019 | Constantin | A61B 5/0024 |
| 2021/0187196 A1* | 6/2021 | Lee | A61M 5/14244 |
| 2021/0187197 A1* | 6/2021 | Zade | A61M 5/1723 |

* cited by examiner

METHODS OF DETERMINING INSULIN INJECTION AMOUNT, COMPUTER STORAGE MEDIUMS AND DEVICES

This application is a U.S. National Stage Application of PCT International Application No. PCT/CN2018/117211 entitled "METHOD OF DETERMINING INSULIN INJECTION AMOUNT, COMPUTER STORAGE MEDIUM AND DEVICE" and filed on Nov. 23, 2018, which claims priority to Chinese Patent Application No. 2018112954926 entitled "METHOD OF DETERMINING INSULIN INJECTION AMOUNT, COMPUTER STORAGE MEDIUM AND DEVICE" and filed on Nov. 1, 2018, the entire contents of each of the foregoing applications are incorporated herein by reference.

FIELD

The present disclosure relates to the field of medical technology, and in particular, to methods of determining insulin injection amount, and computer storage mediums and devices.

BACKGROUND

Diabetes is a common endocrine disease, which refers to abnormal glucose metabolism due to insufficiency (relative or absolute) or excess of insulin. Patients with diabetes generally need to have normal amounts of insulin in their bodies by external means to ensure normal sugar metabolism. Artificial pancreas is an intelligent system which takes the blood glucose monitoring result obtained by the continuous glucose monitoring system as input and the insulin pump injection amount as the output. An insulin injection amount (i.e., an insulin pump injection amount) can be determined by completing the core control algorithm from the input to the output, so as to ensure a long-term blood glucose level for the patient.

However, the approach requires timely blood glucose feedback, the patient needs to have blood glucose monitor equipment to continuously monitor the blood sample in the body. Based on the monitored blood glucose content as input, the output of the insulin pump injection amount (patient injection amount of insulin) is obtained. In other words, the approach must continuously work with the blood glucose monitor device, and the determination of the insulin injection amount is inconvenient.

SUMMARY

According to various embodiments of the present disclosure, methods of determining insulin injection amount, and computer storage mediums and devices are provided.

A method of determining an insulin injection amount includes:
  obtaining characteristic information and a blood glucose content at a current time of a target user; and
  determining an insulin injection amount at each time of the target user based on the characteristic information of the target user, the blood glucose content at the current time of the target user, a predetermined blood glucose prediction model, and a predetermined insulin injection amount prediction model.

One or more non-transitory storage medium storing computer-executable instructions that, when executed by one or more processors, cause the one or more processors to perform the steps of:
  obtaining characteristic information and a blood glucose content at a current time of a target user; and
  determining an insulin injection amount at each time of the target user based on the characteristic information of the target user, the blood glucose content at the current time of the target user, a predetermined blood glucose prediction model, and a predetermined insulin injection amount prediction model.

A computer apparatus, including a memory and a processor, the memory having computer-executable instructions stored therein which, when executed by the processor, causing the processor to perform the steps of:
  obtaining characteristic information and a blood glucose content at a current time of a target user; and
  determining an insulin injection amount at each time of the target user based on the characteristic information of the target user, the blood glucose content at the current time of the target user, a predetermined blood glucose prediction model, and a predetermined insulin injection amount prediction model The details of one or more embodiments of the application are set forth in the accompanying drawings and the description below. Other features and advantages of the application will be apparent from the description, drawings, and claims.

BRIEF DESCRIPTION OF THE DRAWINGS

To illustrate the technical solutions according to the embodiments of the present disclosure or in the prior art more clearly, the accompanying drawings for describing the embodiments or the prior art are introduced briefly in the following. Apparently, the accompanying drawings in the following description are only some embodiments of the present disclosure, and persons of ordinary skill in the art can derive other drawings from the accompanying drawings without creative efforts.

DETAILED DESCRIPTION OF THE EMBODIMENTS

The present disclosure will be described in details in combination with the accompanying drawings and embodiments such that the technical solution and advantages of the present disclosure will be more apparent. It should be understood that the particular embodiments are described for the purpose of illustrating rather than restricting the present disclosure.

Figure 1:
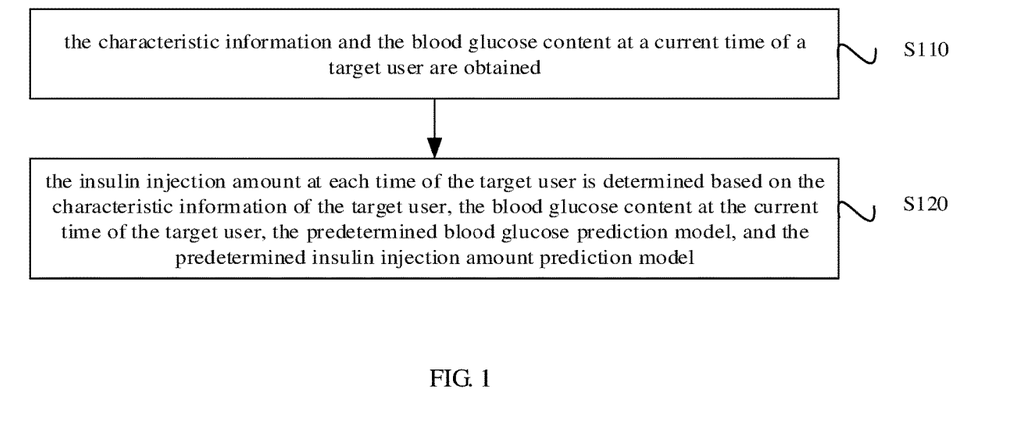
FIG. 1 is a flow chart of a method of determining insulin injection amount according to an embodiment.

In an embodiment, as shown in FIG. 1, a method of determining an insulin injection amount is provided. This embodiment is illustrated primarily by the application of the method to a computer apparatus (i.e., the method is performed by the computer apparatus). In particular, the method of determining the insulin injection amount includes the follow steps:

In step S110: the characteristic information and the blood glucose content at a current time of a target user are obtained.

The characteristic information is the information representing the characteristics of the user, that is, the personal profile of the user can be characterized. The blood glucose content in the user's body is variable, and in the process of predicting the insulin injection amount at each time, it is necessary to obtain the blood glucose content at the current time. In an example, the blood glucose content at the current time may be the average blood glucose content at the current time, i.e., the average of the blood glucose content at the current time and for a preset period of time prior to the current time. For example, the current time is 11 am, there is a corresponding blood glucose content at 11 am, the preset period of time is 1 hour, the blood glucose content at the current time can be understood as the average of the corresponding blood glucose content at 11 am and the blood glucose content within 1 hour before 11 am.

In step S120: the insulin injection amount at each time of the target user is determined based on the characteristic information of the target user, the blood glucose content at the current time of the target user, the predetermined blood glucose prediction model, and the predetermined insulin injection amount prediction model.

The input of the predetermined insulin injection amount prediction model includes the characteristic information and the blood glucose content at an arbitrary time, and the output is the insulin injection amount at the arbitrary time for predicting the insulin injection amount. The input of the predetermined blood glucose prediction model includes characteristic information, the blood glucose content at the arbitrary time, and an insulin injection amount at the arbitrary time, the output is the blood glucose content at the next time corresponding to the arbitrary time (as an input of a predetermined insulin injection amount prediction model in the insulin injection amount prediction process at a next time, so as to realize the insulin injection amount prediction at the next time), that is, for the prediction of blood glucose content.

In an example, the insulin injection amount may be a basal insulin injection amount (insulin basal) or a meal insulin injection amount (insulin bolus).

In an example, after learning the characteristic information and the blood glucose content at the current time of the target user, it may be used as input to the predetermined insulin injection amount prediction model, and in addition, the blood glucose content at the next time predicted and outputted by the predetermined blood sample prediction model may be used as an input to the predetermined insulin injection amount prediction model for predicting the insulin injection amount at the next time.

According to the method of determining insulin injection amount, through the predetermined blood glucose prediction model and the predetermined insulin injection amount prediction model, the insulin injection amount of the target user at different times can be predicted based on the characteristic information and the blood glucose content at the current time of the target user, therefore the insulin injection amount of the target user at each time can be predicted. In the process of predicting the insulin injection amount of the target user, it is possible to use a predetermined insulin injection amount prediction model in combination with a predetermined blood glucose prediction model without performing blood glucose monitoring using a blood glucose monitoring device, so that the insulin injection amount of the target user corresponding to each time can be determined, so as to facilitate the determination of the insulin injection amount.

Figure 2:
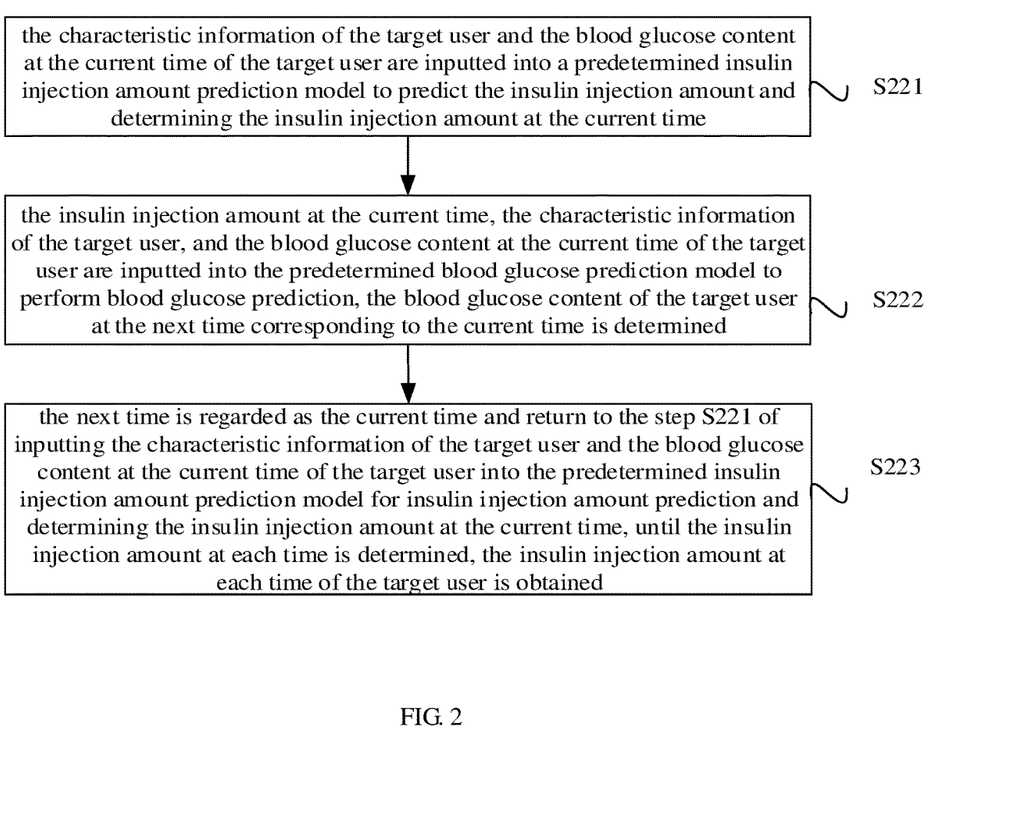
FIG. 2 is a sub-flow chart of the determining an insulin injection amount of a target user at each time according to another embodiment.

As shown in FIG. 2, in an embodiment, the determining the insulin injection amount at each time of the target user includes:

In step S221: the characteristic information of the target user and the blood glucose content at the current time of the target user are inputted into a predetermined insulin injection amount prediction model to predict the insulin injection amount and determining the insulin injection amount at the current time.

That is, the insulin injection of the target user at a time is determined, and the time is the current time. In this embodiment, it is necessary to predict the insulin injection amount at each time. The insulin injection amount of each time is predicted at step S221, the insulin at the current time can be obtained. The insulin injection amount at each time can be understood as the insulin injection amount at each current time. When predicting the insulin injection amount at the current time, the blood sample content at the current time is required as basis, and the insulin injection amount at the current time obtained by the above steps can be used as the basis for the blood glucose prediction for the next time. In case when the blood glucose is not initially predicted, the blood glucose at the current time may be obtained by a blood glucose measurement.

In step S222: the insulin injection amount at the current time, the characteristic information of the target user, and the blood glucose content at the current time of the target user are inputted into the predetermined blood glucose prediction model to perform blood glucose prediction, the blood glucose content of the target user at the next time corresponding to the current time is determined.

The predicted insulin injection amount at the current time is used as a basis for predicting the blood sample content at the next time by a predetermined blood glucose prediction model. That is, in the blood glucose content prediction process at the next time, not only the characteristic information of the target user but also the blood glucose content at the current time of the target user are utilized, furthermore, the insulin injection amount at the current time predicted by the predetermined insulin injection amount prediction model is also utilized.

In step S223: the next time is regarded as the current time and return to the step S221 of inputting the characteristic information of the target user and the blood glucose content at the current time of the target user into the predetermined insulin injection amount prediction model for insulin injection amount prediction and determining the insulin injection amount at the current time, until the insulin injection amount at each time is determined, the insulin injection amount at each time of the target user is obtained.

After the next time is regarded as the current time, it can be understood that the blood glucose content at the current time is updated to the blood glucose content at the next time predicted and outputted by the predetermined blood glucose prediction model, the insulin injection prediction at the current time is re-performed, and the current time is the described next time. The insulin injection amount prediction and the prediction of the blood glucose content at the next time are repeated until the insulin injection amount at each time is determined, and the insulin injection amount by at each time of the target user is obtained.

In an example, each time may be a sampling time within a preset time range, and the interval time between adjacent times among the times may be the same. It can be understood that in a process of the insulin injection amount prediction and the blood glucose content, the difference between the next time and the current time is the time interval, for example, an hour. In another example, the preset time range can be understood as, when this prediction is made by the method of determining insulin injection amount, a time range from the current time corresponding to the process of insulin injection amount prediction performed for the first time via step S221 to 24 hours after the current time, that is, each sampling time point includes the current time.

In an embodiment, an approach of determining a predetermined insulin injection amount prediction model includes:

A marked training set and a unmarked training set are obtained; an initial insulin injection amount prediction model is initialized and obtained; based on the marked training set and unmarked training set, the initial insulin injection amount prediction model is trained and a predetermined insulin injection amount prediction model is determined.

In the process of obtaining the predetermined insulin injection amount prediction model, first, an initial insulin injection amount prediction model needs to be initialized, the parameters in the model are not optimal, the model is trained, and the parameters are continuously optimized to determine the optimal parameters to obtain the predetermined insulin injection prediction model. In this embodiment, the initial insulin injection amount prediction model is trained by the marked training set and the unmarked training set to improve the accuracy of the predetermined insulin injection prediction model. The marked training set includes characteristic information, a blood glucose content at each sampling time, and an insulin injection amount at each sampling time of each first-sample user. The unmarked training set includes the characteristic information and the blood glucose content at each sampling time of each second-sample user. It can be understood that the unmarked training set has no insulin injection amount at each sampling time corresponding to each second-sample user, and the marked training set has insulin injection amount at each sampling time of each first-sample user. Based on the marked training set and the unmarked training set, the obtained predetermined insulin injection amount prediction model is a semi-supervised predetermined insulin injection amount prediction model.

In an example, the obtaining the blood glucose content at each sampling time includes obtaining a continuous blood glucose content (e.g., a blood glucose content profile recorded by a blood glucose monitoring device); sampling the continuous blood glucose content to obtain a blood sample content at each sampling time. For the process of obtaining the blood glucose content of each first-sample user at each sampling time, the continuous blood glucose content is the continuous blood glucose content corresponding to each first-sample user, that is, each continuous blood glucose content needs to be sampled separately. Similarly, for the process of obtaining the blood glucose content of each second-sample user at each sampling time, the continuous blood glucose content is the continuous blood glucose content corresponding to each second-sample user, that is, each continuous blood glucose content needs to be sampled separately.

Figure 3:
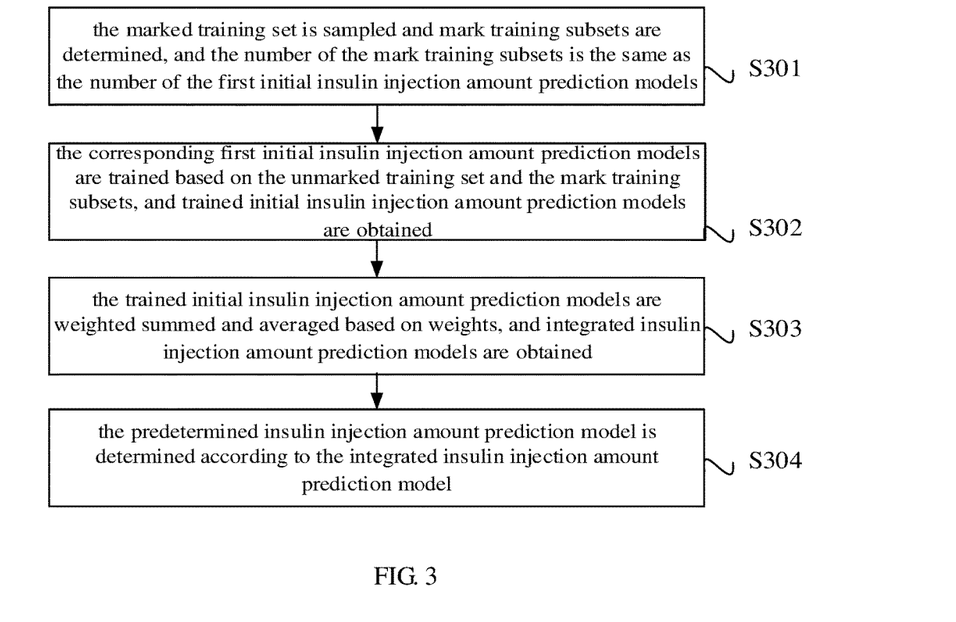
FIG. 3 is a sub-flow chart of the determining a predetermined insulin injection amount prediction model according to another embodiment.

As shown in FIG. 3, in an embodiment, the initial insulin injection amount prediction model includes each first initial insulin injection amount prediction model.

The determining the predetermined insulin injection amount prediction model includes:

In step S301: the marked training set is sampled and mark training subsets are determined, and the number of the mark training subsets is the same as the number of the first initial insulin injection amount prediction models.

That is, a preset number of times of sampling can be performed to the marked training set, and the preset number of times is the same as the number of the first initial insulin injection amount prediction models, and the mark training subsets are obtained. The mark training subsets include characteristic information, a blood glucose content at each sampling time, and an insulin injection amount at each sampling time of some sample users of the first-sample users. The sample users in the mark training subsets obtained in each sampling may be different. In an example, the numbers of sample users in each mark training subset are the same, i.e., the number of sample users obtained in each sampling is the same. As such, the resulting subset of mark training can be used as a training basis for the corresponding first initial insulin injection amount prediction model to ensure equalization of data size.

In step S302: the corresponding first initial insulin injection amount prediction models are trained based on the unmarked training set and the mark training subsets, and trained initial insulin injection amount prediction models are obtained.

A mark training subset is an input to a corresponding first initial insulin injection amount prediction model for training, such that training of each first initial insulin injection amount prediction model can be achieved using each mark training subset, thereby obtaining the trained initial insulin injection amount prediction models.

In step S303: the trained initial insulin injection amount prediction models are weighted summed and averaged based on weights, and integrated insulin injection amount prediction models are obtained.

In step S304: the predetermined insulin injection amount prediction model is determined according to the integrated insulin injection amount prediction model.

The trained initial insulin injection amount prediction models are weighted summed and averaged based on the weights, and it is understood that the outputs of the trained initial insulin injection amount prediction models are weighted summed and averaged. The trained initial insulin injection amount prediction models may perform insulin injection amount prediction, and in order to improve the prediction accuracy, the outputs of trained initial insulin injection amount prediction models may be weighted summed and averaged according to the weights to obtain the integrated insulin injection amount prediction model. Then the predetermined insulin injection amount prediction model is determined based on the integrated insulin injection amount prediction model, thereby improving the accuracy of the predetermined insulin injection amount prediction model.

In an embodiment, the step S304 of determining the predetermined insulin injection amount prediction model according to the integrated insulin injection amount prediction model includes:

The weights in the integrated insulin injection amount prediction model is adjusted based on the marked training set and determining the predetermined insulin injection amount prediction model.

The above weights can be obtained by pre-initialization, and the size of the weight affects the accuracy of the prediction performed by the integrated insulin injection amount prediction model, thereby affecting the prediction accuracy of the predetermined insulin injection amount prediction model. In the present embodiment, the weights in the integrated insulin injection amount prediction model are adjusted using a marked training set to obtain the target weights. The predetermined insulin injection amount prediction model is an updated integrated insulin injection amount prediction model obtained by respectively updating the weights in the integrated insulin injection amount prediction model to the corresponding target weights. It can be understood that the integrated insulin injection amount prediction model is trained based on the marked training set to realize adjustment of the weights, that is, the integrated insulin injection amount prediction model is trained based on the marked training set and target weights are determined, the trained integrated insulin injection amount prediction model can be understood as the predetermined insulin injection amount prediction model.

In an embodiment, the determining the predetermined blood glucose prediction model includes: a sample marked training set is obtained; the initial blood glucose prediction model is initialized and obtained; the initial blood glucose prediction model is trained based on the marked training set, and the predetermined blood glucose prediction model is determined.

In the process of obtaining the predetermined blood glucose prediction model, firstly, an initial blood glucose prediction model needs to be initialized, the parameters in the model are not optimal, the model is trained, the parameters are continuously optimized, and the optimal parameters are determined, thereby the above predetermined insulin injection prediction model is obtained. In this embodiment, the initial blood glucose prediction model is trained by a sample marked training set. The sample mark training set includes characteristic information, a blood glucose content at each sampling time, and an insulin injection amount at each sampling time of each third sample user. It can be understood that the training data in the sample marked training set is marked, i.e., there is the insulin injection amount at each sampling time corresponding to the sample user. The predetermined blood glucose prediction model obtained based on the sample mark training is the predetermined supervised blood glucose prediction model.

In an embodiment, the characteristic information includes clinical information as well as dietary information, the clinical information may include height, weight, fasting blood glucose content, and connecting peptide content.

The clinical information and the dietary information are relatively easy-to-obtain data to assist the insulin injection amount prediction model, so as to ensure the accuracy of the prediction, without the trouble of accumulating a large amount of data. In an example, the dietary information may include an eating condition, and the connecting peptide content may be a connecting peptide content after 2 hours of eating. In an example, the dietary information is the dietary information at the current time, and if the next time is regarded as the current time, the dietary information at the current time is the dietary information at the next time.

Hereinafter, the method of determining the insulin injection amount will be described in detail with a specific embodiment. The method realizes automatic analysis and generation of an insulin injection amount over 24 hours or longer by constructing a blood glucose prediction model based on supervised learning and an insulin injection amount prediction model based on semi-supervised learning. The specific process is as follows:

First of all, the model training.

Data cleaning and screening and pre-processing are performed to the marked data with clinical information (such as height, weight, fasting blood glucose content and C-peptide after 2 hours), dietary information (such as breakfast intake, etc.), and time information (such as current time of hours and minutes), continuous blood glucose information (such as a blood glucose profile recorded by a continuous blood glucose monitoring device), and corresponding insulin injection amount (e.g. insulin basal or bolus injection amount) and the unmarked data with the above clinical information, dietary information, time information, and continuous blood glucose information but without the insulin injection amount are data cleaning screening and pre-treatment. The marked data is divided into a marked training set and a marked test set.

Figure 4:
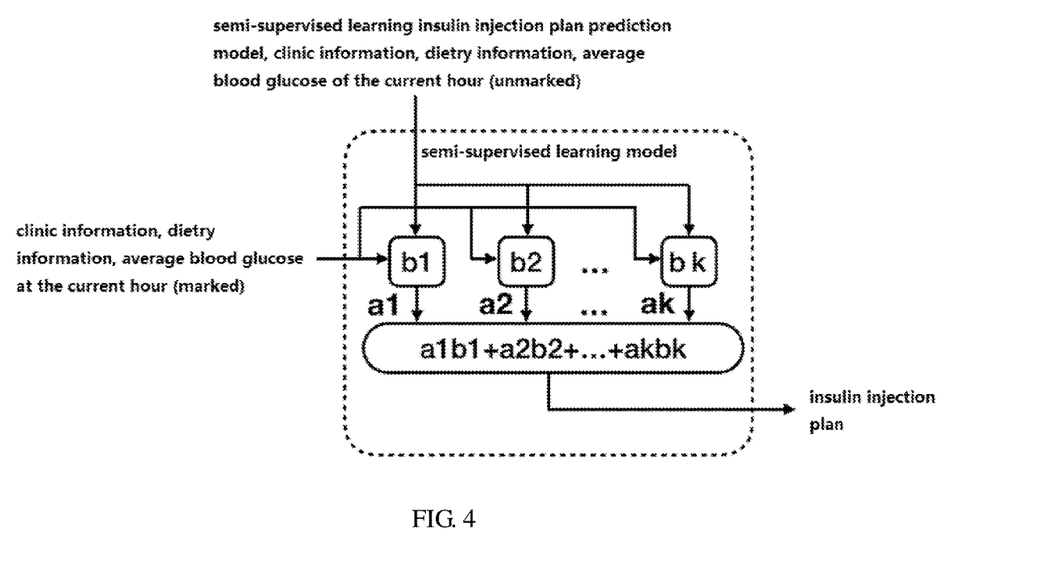
FIG. 4 is a schematic diagram of determining an insulin injection amount prediction model according to another embodiment.

As shown in FIG. 4, the injection schedule corresponds to the injection amount, and the blood glucose content is the average blood sample. An insulin injection amount prediction model based on semi-supervised learning is constructed, in which the clinical information, the current time and its corresponding dietary information, and the blood glucose content at the current time are inputted, and the insulin injection amount at the current time is outputted. The same number of pieces of partial data are extracted from the marked training set for several times to form the mark training subsets, using the mark training subsets as the marked training set for a semi-supervised learner (corresponding to the first initial insulin injection amount prediction model described above), using all the unmarked data as the unmarked training set, each mark training subset correspondingly trains a semi-supervised learner, the time is in hours, i.e. the time interval between the current time and the next time is 1 hour. The trained semi-supervised learner is constructed into an integrated semi-supervised model (i.e., the integrated insulin injection amount prediction model described above) by weighted summing and averaging. In turn, the weights in the integrated semi-supervised model is adjusted using a marked training set and the predetermined insulin injection amount prediction model is determined. In particular, the mark training set is used to train a corresponding supervised learner, the weight of each semi-supervised learner is continuously adjusted under the condition that the predicted result of the supervised learner is taken as a baseline, until a value exceeding the result of supervised learning is obtained. Finally, this integrated semi-supervised learning model is regarded as the final prediction model of insulin injection amount. b1 is the first semi-supervised learner, b2 is the second semi-supervised learner, bk is the k-th semi-supervised learner, a1 is the weight corresponding to the first semi-supervised learner, a2 is the weight corresponding to the second semi-supervised learner, and ak is the weight corresponding to the k-th semi-supervised learner.

At the time of the test, the insulin injection amount at the current time of the patient is obtained using the clinical information, the current time and its corresponding dietary information, and the blood glucose content input model at the current time in the marked test set.

Figure 5:
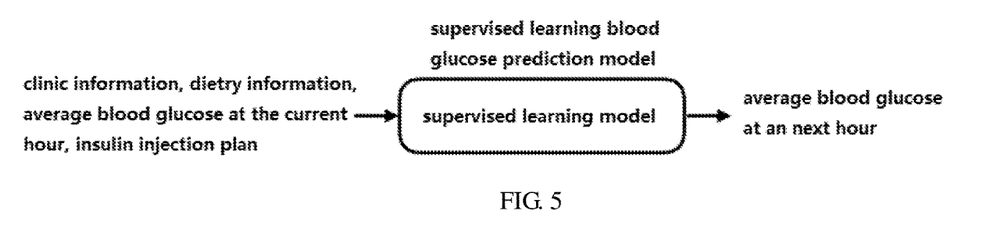
FIG. 5 is a schematic diagram of determining a blood glucose prediction model according to another embodiment.

As shown in FIG. 5, a blood glucose prediction model based on supervised learning is constructed with the clinical information, the current time and its corresponding dietary information, the insulin injection amount at the current time, and the blood glucose content (specifically, the average blood glucose) at the current time as inputs, and the blood glucose content (which may be the average blood glucose) at the next time as output. The marked training set is used for training and cross validation is performed. At the time of test, clinical information, the current time and its corresponding dietary information, and the blood glucose content at the current time in the marked test set, and the insulin treatment schedule at the current time obtained from the insulin injection amount prediction model are inputted into the blood glucose prediction model to obtain the average blood glucose of the patient at the next time.

Then, the model prediction.

1) the clinical information, the current time and its corresponding dietary information and the average blood glucose at the current time are inputted into the insulin injection amount prediction model to obtain an insulin injection amount at the current time;

2) the clinical information, the current time and its corresponding dietary information, the average blood glucose at the current time, as well as and the insulin injection amount at the current time obtained in 1) are inputted into the blood glucose prediction model again, the blood glucose content (average blood glucose) at the next time is obtained; and 3) 1) and 2) are continuously repeated, and an insulin injection prediction over 24 hour or longer can be obtained.

Specifically, for a patient, in his current time, the insulin injection amount at the current time is first predicted using the corresponding clinical information, the dietary information corresponding to the current time, and the blood glucose content (average blood glucose) at the current time. The clinical information, the dietary information corresponding to the current time, the blood glucose content at the current time, and the insulin injection amount at the current time obtained in the previous step are used to predict the average blood glucose at the next time. Thereafter, the clinical information, the dietary information at the next time, and the average blood glucose at the next time obtained from the previous step are used to predict the insulin injection amount at the next time corresponding to the next time, the repetition goes on and on, an insulin injection amount over a period of time can be obtained.

Figure 6:
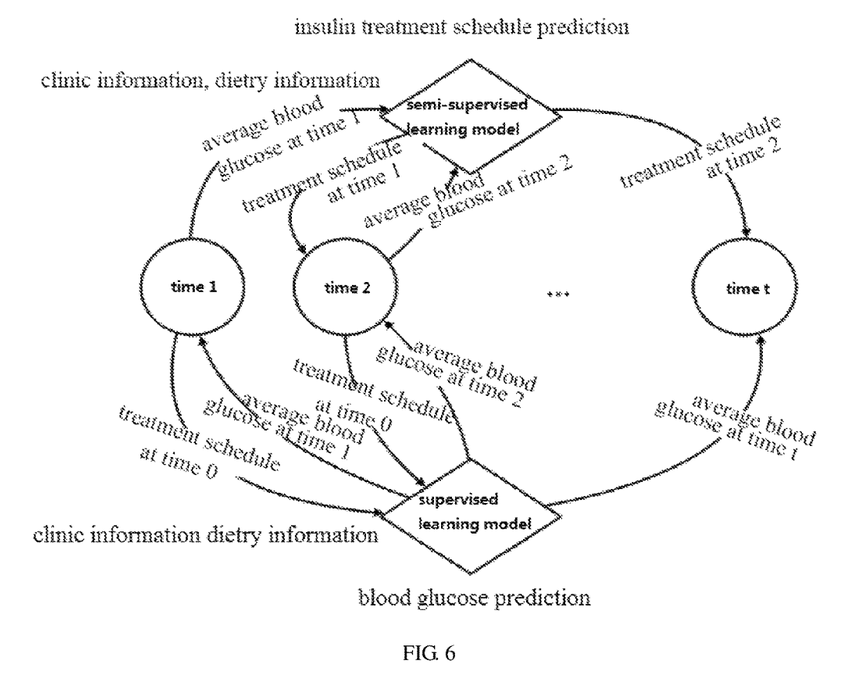
FIG. 6 is a schematic diagram of determining an insulin injection amount of a target user at each time according to another embodiment.

For example, as shown in FIG. 6, the semi-supervised learning model corresponds to the insulin injection amount prediction model, and the supervised learning model corresponds to the blood glucose prediction model, and the treatment schedule is the insulin injection amount. The supervised learning model predicts the treatment schedule at time 1 utilizing the treatment schedule at time 0, the clinical information and dietary information at time 0, and use the predicted treatment schedule at time 1 as an input to a semi-supervised learning model. The semi-supervised learning model utilizes the average blood glucose at time 1, the clinical information and dietary information at time 1 to predict the treatment schedule at time 1 and inputs the predicted treatment schedule at time 1 to a supervised learning model. The supervised learning model performs prediction according to the treatment schedule at time 1, the clinical information and the dietary information at time 1, and the average blood glucose at time 2, the result of the prediction is used as an input to the semi-supervised learning model. The semi-supervised learning model utilizes the average blood glucose at time 2, the clinical information and dietary information at time 2 to predict the treatment schedule at time 2 and inputs the predicted treatment schedule at time 2 to the supervised learning model. The repetition goes on, until the semi-supervised learning model predicts and obtains the treatment schedule at time t−1, and inputs the treatment schedule at time t−1 to the supervised learning model. The supervised learning model can predict the average blood glucose at time t through the treatment schedule at t−1, the clinical information and dietary information at time t−1. As such, the insulin injection amount of the patient at time 1, time 2 . . . time t−1 can be determined.

According to the method of determining the insulin injection amount, a blood glucose side model is constructed utilizing the existing data of continuous blood glucose content monitoring of a patient to assist the insulin injection amount prediction. In addition to improve the prediction accuracy, a relatively accurate prediction of blood glucose level can be provided for patients with no blood glucose monitoring data without additional equipment for blood glucose monitoring, which improves the convenience greatly. That is, a relatively accurate blood glucose prediction model can be established using massive existing patient blood glucose detection data, and the prediction result of the blood glucose prediction model can be used to assist the accurate generation of the insulin injection amount. For the patient who finally uses the blood glucose prediction model and the insulin injection amount prediction model, a more accurate insulin injection amount can be obtained without wearing a continuous blood glucose monitoring device for test and experiment, which facilitates the determination of the insulin injection amount.

In addition, the insulin injection amount prediction model used a semi-supervised learn approach and massive relatively easy-to-obtain clinical information and dietary information to assist the insulin injection amount prediction. It not only ensures the accuracy of prediction, but also saves the trouble of accumulating a large amount of data.

In addition, in the process of the insulin injection amount prediction of each patient, the relevant clinical information of the patient is included in the data characteristics, that is, the clinical baseline characteristics of the patient is taken into account each time in the blood glucose prediction and the insulin injection amount prediction, which is a patient-specific insulin injection amount prediction. This provides the method greater adaptability to different patients.

Figure 7:
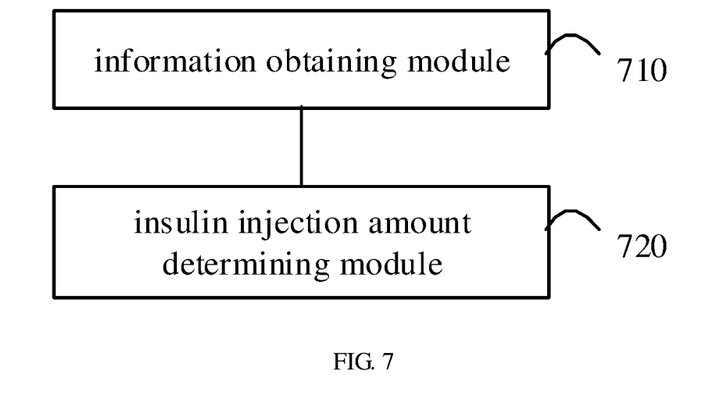
FIG. 7 is a block diagram of an apparatus of determining insulin injection amount according to an embodiment.

As shown in FIG. 7, in an embodiment, an apparatus of determining insulin injection amount is provided, which may be provided in a computer apparatus and includes an information obtaining module 710 and an insulin injection amount determining module 720.

An information obtaining module 710, configured to obtain characteristic information and a blood glucose content at a current time of a target user.

An insulin injection amount determining module 720, configured to determine an insulin injection amount at each time of the target user based on the characteristic information of the target user, the blood glucose content at the current time of the target user, a predetermined blood glucose prediction model, and a predetermined insulin injection amount prediction model.

In an embodiment, the insulin injection amount determining module 720 includes an insulin injection amount predicting module, a blood glucose predicting module, and an insulin injection amount obtaining module.

The insulin injection amount predicting module is configured to input the characteristic information of the target user and the blood glucose content at the current time of the target user into the predetermined insulin injection amount prediction model to predict the insulin injection amount and determine the insulin injection amount at the current time.

The blood glucose predicting module is configured to input the insulin injection amount at the current time, the characteristic information of the target user, and the blood glucose content at the current time of the target user into the predetermined blood glucose prediction model to perform blood glucose prediction, and determine a blood glucose content of the target user at a next time corresponding to the current time; and The insulin injection amount obtaining module is configured to regard the next time as the current time and returning to the inputting the characteristic information of the target user and the blood glucose content at the current time of the target user into the predetermined insulin injection amount prediction model to predict the insulin injection amount and determining the insulin injection amount at the current time; until the insulin injection amount at each time is determined, and obtaining a respective corresponding insulin injection amount at each time of the target user.

In an embodiment, the apparatus further includes a training set obtaining module, an insulin injection amount model initializing module, and an insulin injection amount prediction model determining module.

The training set obtaining module is configured to obtain a marked training set and a unmarked training set, the marked training set includes the characteristic information, the blood glucose content of each first-sample user at each sampling time, and the insulin injection amount of each first-sample user at each sampling time; the unmarked training set includes characteristic information and a blood glucose content of each second-sample user at each sampling time;

The insulin injection amount model initializing module is configured to initialize and obtain the an initial insulin injection amount prediction model;

The insulin injection amount prediction model determining module is configured to train the initial insulin injection amount prediction model based on the marked training set and the unmarked training set and determining the predetermined insulin injection amount prediction model.

In an embodiment, the initial insulin injection amount prediction model includes first initial insulin injection amount prediction models;

The insulin injection amount prediction model determining module includes a sampling module, an insulin injection amount prediction model training module, a weighting module, and a model obtaining module.

The sampling module is configured to sample the marked training set and determining mark training subsets, the number of the mark training subsets is the same as the number of the first initial insulin injection amount prediction models;

The insulin injection amount prediction model training module is configured to train the corresponding first initial insulin injection amount prediction model based on the unmarked training set and the mark training subsets to obtain trained initial insulin injection amount prediction models;

The weighting module is configured to perform weighted summation and averaging on each of the trained initial insulin injection amount prediction models based on weights, and obtaining an integrated insulin injection amount prediction model; and The model obtaining module is configured to determine the predetermined insulin injection amount prediction model according to the integrated insulin injection amount prediction model.

In an embodiment, the model obtaining module includes an adjustment module, a model obtaining module, a sample training set obtaining module, a blood glucose prediction model initializing module, and a blood glucose prediction model training module.

The adjustment module is configured to adjust each of the weights in the integrated insulin injection amount prediction model based on the marked training set and determining the predetermined insulin injection amount prediction model.

The model obtaining module, the apparatus further includes:

The sample training set obtaining module is configured to obtain a sample marked training set; the sample marked training set includes characteristic information, a blood glucose content at each sampling time, and an insulin injection amount at each sampling time of each third sample user;

The blood glucose prediction model initializing module is configured to initialize and obtain an initial blood glucose prediction model; and The blood glucose prediction model training module is configured to train the initial blood glucose prediction model based on the marked training set and determining the predetermined blood glucose prediction model.

In an embodiment, the characteristic information includes clinical information and dietary information, the clinical information includes height, weight, fasting blood glucose content, and connecting peptide content.

The technical features in the apparatus of determining insulin injection amount respectively correspond to those in the method of determining insulin injection amount and are omitted for brevity.

Figure 8:
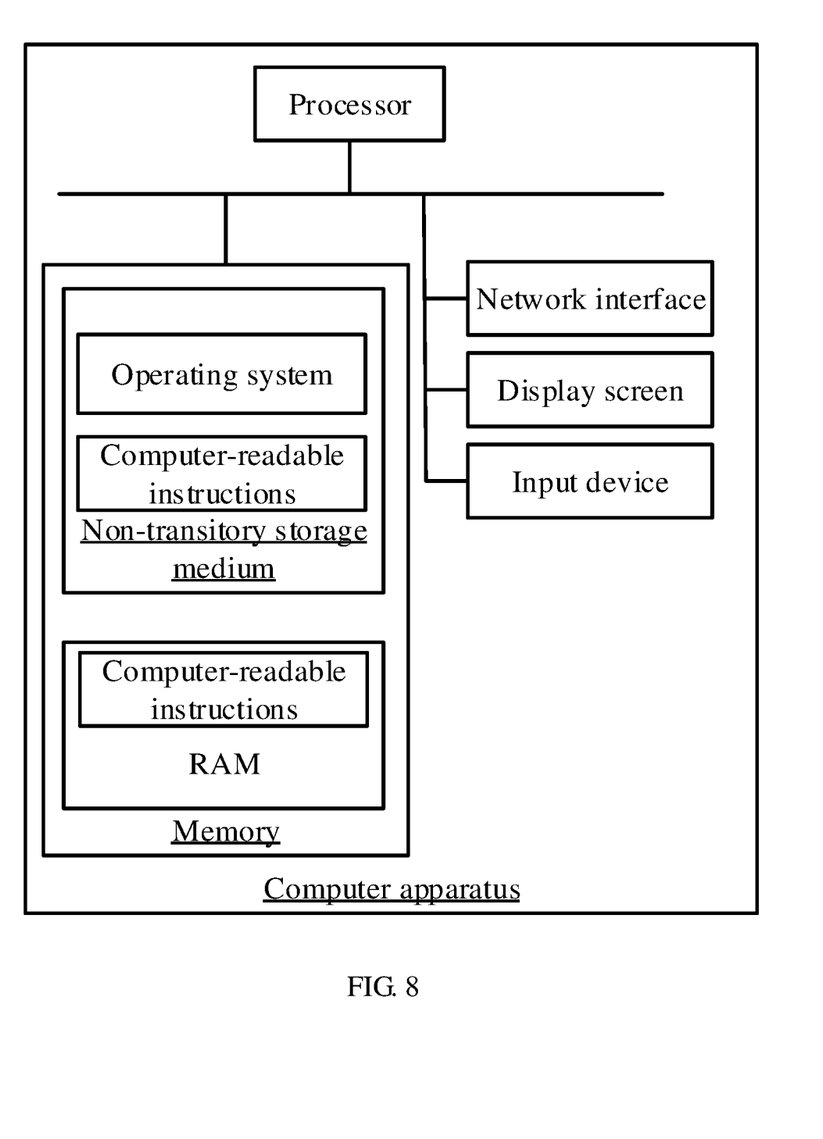
FIG. 8 is a block diagram of a computer apparatus in an embodiment.

FIG. 8 is a schematic diagram of a computer apparatus according to an embodiment. The computer apparatus includes a processor, a memory, and a network interface. The memory of the computer apparatus includes a non-transitory storage medium and a Random Access Memory (RAM). The non-transitory storage medium has an operating system and computer-executable instructions stored thereon which, when executed by the processor, cause the processor to implement the method of determining insulin injection amount. The RAM also has computer-executable instructions stored therein which, when executed by the processor, cause the processor to implement the method of determining insulin injection amount. In an embodiment, the computer apparatus further includes a display screen and an input device, the display screen of the computer apparatus may be a liquid crystal display screen or an electronic ink display screen, and the input device of the computer apparatus may be a touch layer covered on the display screen, or be a key, a trackball or a touch pad set on the housing of the computer apparatus, or may be an external keyboard, touch pad or mouse.

It will be understood by those skilled in the art that the structure shown in FIG. 8 is merely a block diagram of a portion of the structure associated with the present application scheme and does not constitute a limitation on the computer apparatus to which the present application scheme is applied, the particular computer apparatus may include more or fewer components than shown in the diagram, or in combination with certain components, or with a different arrangement of components.

In an embodiment, the apparatus of determining insulin injection amount provided herein may be implemented in the form of a computer program that may be run on a computer apparatus as shown in FIG. 8. The non-transitory storage medium of the computer apparatus may store various program modules constituting the apparatus of determining insulin injection amount, such as the information obtaining module 710 and the insulin injection amount determining module 720 shown in FIG. 7. The program modules include computer-executable instructions which are configured to cause the computer apparatus to perform steps in the method of determining insulin injection amount according to various embodiments described in the specification of the present application. For example, the computer apparatus may obtain the characteristic information and the blood glucose content at the current time of the target user through the information obtaining module 710 shown in FIG. 7, and based on the characteristic information of the target user, the blood glucose content at the current time of the target user, the predetermined blood glucose prediction model, and the predetermined insulin injection amount prediction model, through the insulin injection amount determining module 720, the insulin injection amount at each time of the target user is determined.

In an embodiment, a computer apparatus is provided, which includes a memory and a processor, the memory has computer-executable instructions stored therein which, when executed by the processor, causes the processor to provide the steps of: obtaining characteristic information and a blood glucose content at a current time of a target user; and determining an insulin injection amount at each time of the target user based on the characteristic information of the target user, the blood glucose content at the current time of the target user, a predetermined blood glucose prediction model, and a predetermined insulin injection amount prediction model.

In an embodiment, the determining the insulin injection amount at each time of the target user includes: inputting the characteristic information of the target user and the blood glucose content at the current time of the target user into the predetermined insulin injection amount prediction model to predict the insulin injection amount and determining the insulin injection amount at the current time; inputting the insulin injection amount at the current time, the characteristic information of the target user, and the blood glucose content at the current time of the target user into the predetermined blood glucose prediction model to perform blood glucose prediction, and determining a blood glucose content of the target user at a next time corresponding to the current time; and regarding the next time as a current time and returning to the inputting the characteristic information of the target user and the blood glucose content at the current time of the target user into the predetermined insulin injection amount prediction model to predict the insulin injection amount and determining the insulin injection amount at the current time; until the insulin injection amount at each time is determined, and obtaining the respective corresponding insulin injection amount at each time of the target user.

In an embodiment, the determining the predetermined insulin injection amount prediction model includes: obtaining a marked training set and a unmarked training set, the marked training set includes the characteristic information, the blood glucose content of each first-sample user at each sampling time, and the insulin injection amount of each first-sample user at each sampling time; the unmarked training set includes characteristic information and a blood glucose content of each second-sample user at each sampling time; initializing and obtaining the an initial insulin injection amount prediction model; and training the initial insulin injection amount prediction model based on the marked training set and the unmarked training set and determining the predetermined insulin injection amount prediction model.

In an embodiment the initial insulin injection amount prediction model includes first initial insulin injection amount prediction models;

The determining the predetermined insulin injection amount prediction model includes: sampling the marked training set and determining mark training subsets, the number of the mark training subsets is the same as the number of the first initial insulin injection amount prediction models; training the corresponding first initial insulin injection amount prediction model based on the unmarked training set and the mark training subsets to obtain trained initial insulin injection amount prediction models; performing weighted summation and averaging on each of the trained initial insulin injection amount prediction models based on weights, and obtaining an integrated insulin injection amount prediction model; and determining the predetermined insulin injection amount prediction model according to the integrated insulin injection amount prediction model.

In an embodiment, the determining the predetermined insulin injection amount prediction model according to the integrated insulin injection amount prediction model includes: adjusting each of the weights in the integrated insulin injection amount prediction model based on the marked training set and determining the predetermined insulin injection amount prediction model.

In an embodiment, the determining the predetermined blood glucose prediction model includes: obtaining a sample marked training set; the sample marked training set includes characteristic information, a blood glucose content at each sampling time, and an insulin injection amount at each sampling time of each third sample user; initializing and obtaining an initial blood glucose prediction model; and training the initial blood glucose prediction model based on the marked training set and determining the predetermined blood glucose prediction model.

In an embodiment, the characteristic information includes clinical information and dietary information, wherein the clinical information includes height, weight, fasting blood glucose content, and connecting peptide content.

A storage medium stores computer-executable instructions that, when executed by one or more processors, causes the one or more processors to perform the steps of: obtaining characteristic information and a blood glucose content at a current time of a target user; and determining an insulin injection amount at each time of the target user based on the characteristic information of the target user, the blood glucose content at the current time of the target user, a predetermined blood glucose prediction model, and a predetermined insulin injection amount prediction model.

In an embodiment, the determining the insulin injection amount at each time of the target user includes: inputting the characteristic information of the target user and the blood glucose content at the current time of the target user into the predetermined insulin injection amount prediction model to predict the insulin injection amount and determining the insulin injection amount at the current time; inputting the insulin injection amount at the current time, the characteristic information of the target user, and the blood glucose content at the current time of the target user into the predetermined blood glucose prediction model to perform blood glucose prediction, determining a blood glucose content of the target user at a next time corresponding to the current time; and regarding the next time as a current time and returning to the inputting the characteristic information of the target user and the blood glucose content at the current time of the target user into the predetermined insulin injection amount prediction model to predict the insulin injection amount and determining the insulin injection amount at the current time; until the insulin injection amount at each time is determined, and obtaining the respective corresponding insulin injection amount at each time of the target user.

In an embodiment, the determining the predetermined insulin injection amount prediction model includes: obtaining a marked training set and a unmarked training set, the marked training set includes the characteristic information, the blood glucose content of each first-sample user at each sampling time, and the insulin injection amount of each first-sample user at each sampling time; the unmarked training set includes characteristic information and a blood glucose content of each second-sample user at each sampling time; initializing and obtaining the an initial insulin injection amount prediction model; and training the initial insulin injection amount prediction model based on the marked training set and the unmarked training set and determining the predetermined insulin injection amount prediction model.

In an embodiment, the initial insulin injection amount prediction model includes first initial insulin injection amount prediction models; the determining the predetermined insulin injection amount prediction model includes: sampling the marked training set and determining mark training subsets, the number of the mark training subsets is the same as the number of the first initial insulin injection amount prediction models; training the corresponding first initial insulin injection amount prediction model based on the unmarked training set and the mark training subsets to obtain trained initial insulin injection amount prediction models; performing weighted summation and averaging on each of the trained initial insulin injection amount prediction models based on weights, and obtaining an integrated insulin injection amount prediction model; and determining the predetermined insulin injection amount prediction model according to the integrated insulin injection amount prediction model.

In an embodiment, the determining the predetermined insulin injection amount prediction model according to the integrated insulin injection amount prediction model includes: adjusting each of the weights in the integrated insulin injection amount prediction model based on the marked training set and determining the predetermined insulin injection amount prediction model.

In an embodiment, the determining the predetermined blood glucose prediction model comprises: obtaining a sample marked training set; the sample marked training set includes characteristic information, a blood glucose content at each sampling time, and an insulin injection amount at each sampling time of each third sample user; initializing and obtaining an initial blood glucose prediction model; and training the initial blood glucose prediction model based on the marked training set and determining the predetermined blood glucose prediction model.

In an embodiment, the characteristic information includes clinical information and dietary information, wherein the clinical information includes height, weight, fasting blood glucose content, and connecting peptide content.

It should be understood that although the steps are sequentially displayed as indicated by arrows, these steps are not necessarily sequentially performed as indicated by arrows. Unless explicitly stated herein, the execution of these steps is not strictly sequential, and the steps may be performed in other sequences. Moreover, at least a part of the steps may include a plurality of sub-steps or stages that are not necessarily performed at the same time, but may be performed at different times, and the order of execution of the sub-steps or stages is not necessarily performed sequentially, but may be performed in turn or alternately with at least a part of other steps or sub-steps or stages of other steps.

Persons of ordinary skill in the art understand that all or part of the processes in the methods of the foregoing embodiments may be implemented by a computer program instructing relevant hardware. The computer program may be stored in a non-transitory computer-executable storage medium. When the computer program is executed, flows of embodiments of the methods as described above may be included. Any references to memory, storage, databases, or other media used in the various embodiments provided herein may include non-transitory and/or transitory memory. The non-transitory memory may include a read only memory (ROM), a programmable ROM (PROM), an electrically programmable ROM (EPROM), an electrically erasable programmable ROM (EEPROM), or a flash memory. The transitory memory may include a random access memory (RAM) or an external cache memory. By way of illustration and not limitation, RAM is available in a variety of forms such as static RAM (SRAM), dynamic RAM (DRAM), synchronous DRAM (SDRAM), double data rate SDRAM (DDRSDRAM), enhanced SDRAM (ESDRAM), Synchronous Link DRAM (SLDRAM), Memory Bus (Rambus) Direct RAM (RDRAM), Direct Memory Bus Dynamic RAM (DRDRAM), Memory Bus Dynamic RAM (RDRAM) etc.

The foregoing respective technical features involved in the respective embodiments can be combined arbitrarily, for brevity, not all possible combinations of the respective technical features in the foregoing embodiments are described, however, to the extent they have no collision with each other, the combination of the respective technical features shall be considered to be within the scope of the description.

The foregoing implementations are merely specific embodiments of the present disclosure, and are not intended to limit the protection scope of the present disclosure. It should be noted that any variation or replacement readily figured out by persons skilled in the art within the technical scope disclosed in the present disclosure shall all fall into the protection scope of the present disclosure. Therefore, the protection scope of the present disclosure shall be object to the protection scope of the claims.

What is claimed is:

1. A method comprising:
   determining an insulin injection amount by:
      obtaining, with a computer apparatus, characteristic information and a blood glucose content at a current time of a target user through the computer apparatus, the characteristic information comprising clinical information and dietary information, wherein the clinical information comprises height, weight, fasting blood glucose content, and connecting peptide content;
      determining, with the computer apparatus, an insulin injection amount at each time of a plurality of times after the current time of the target user through the computer apparatus and based on the characteristic information of the target user, the blood glucose content at the current time of the target user, a predetermined blood glucose prediction model, and a predetermined insulin injection amount prediction model; and outputting, with the computer apparatus, the determined insulin injection amount at each time of the plurality of times after the current time of the target user through the computer apparatus; and administering the insulin injection amount to the target user without the target user wearing a continuous blood glucose monitoring device;

wherein the determining the insulin injection amount at each time of the target user comprises:

inputting the characteristic information of the target user and the blood glucose content at the current time of the target user into the predetermined insulin injection amount prediction model to predict the insulin injection amount and determining the insulin injection amount at the current time;

inputting the insulin injection amount at the current time, the characteristic information of the target user, and the blood glucose content at the current time of the target user into the predetermined blood glucose prediction model to perform blood glucose prediction, and determining a blood glucose content of the target user at a next time corresponding to the current time; and regarding the next time as a current time and returning to the inputting the characteristic information of the target user and the blood glucose content at the current time of the target user into the predetermined insulin injection amount prediction model to predict the insulin injection amount and determining the insulin injection amount at the current time; until the insulin injection amount at each time is determined, and obtaining the respective corresponding insulin injection amount at each time of the target user;

wherein determining an insulin injection amount further comprises:

obtaining, with the computer apparatus, a marked training set and a unmarked training set, the marked training set comprising the characteristic information, the blood glucose content of each first-sample user at each sampling time, and the insulin injection amount of each first-sample user at each sampling time; the unmarked training set comprising characteristic information and a blood glucose content of each second-sample user at each sampling time;

initializing and obtaining, with the computer apparatus, an initial insulin injection amount prediction model; and training, with the computer apparatus, the initial insulin injection amount prediction model based on the marked training set and the unmarked training set, and determining the predetermined insulin injection amount prediction model;

wherein the initial insulin injection amount prediction model comprises first initial insulin injection amount prediction models;

wherein the determining the predetermined insulin injection amount prediction model comprises:

sampling, with computer apparatus, the marked training set and determining mark training subsets, wherein the number of the mark training subsets is the same as the number of the first initial insulin injection amount prediction models, the mark training subset comprising the characteristic information, the blood glucose content at each sampling time, and the insulin injection amount at each sampling time of some sample users of the first-sample users;

training, with computer apparatus, the corresponding first initial insulin injection amount prediction model based on the unmarked training set and the mark training subsets to obtain trained initial insulin injection amount prediction models;

performing weighted summation and averaging, with computer apparatus, on each of the trained initial insulin injection amount prediction models based on weights, and obtaining an integrated insulin injection amount prediction model; and determining, with computer apparatus, the predetermined insulin injection amount prediction model according to the integrated insulin injection amount prediction model;

wherein the determining the predetermined insulin injection amount prediction model according to the integrated insulin injection amount prediction model comprises adjusting, with computer apparatus, each of the weights in the integrated insulin injection amount prediction model based on the marked training set, and determining the predetermined insulin injection amount prediction model; and wherein the determining the predetermined blood glucose prediction model comprises:

obtaining, with computer apparatus, a sample marked training set; the sample marked training set comprising characteristic information, a blood glucose content at each sampling time, and an insulin injection amount at each sampling time of each third sample user;

initializing and obtaining, with computer apparatus, an initial blood glucose prediction model; and training, with computer apparatus, the initial blood glucose prediction model based on the marked training set, and determining the predetermined blood glucose prediction model.

2. The method of determining an insulin injection amount according to claim 1, wherein the insulin injection amount comprises a basal insulin injection amount or a meal insulin injection amount.

3. One or more non-transitory storage medium storing computer-executable instructions that, when executed by one or more processors, cause the one or more processors to perform a method comprising:

obtaining characteristic information and a blood glucose content at a current time of a target user through a computer apparatus, the characteristic information comprising clinical information and dietary information, wherein the clinical information comprises height, weight, fasting blood glucose content, and connecting peptide content;

determining an insulin injection amount at each time of a plurality of times after the current time of the target user through the computer apparatus and based on the characteristic information of the target user, the blood glucose content at the current time of the target user, a predetermined blood glucose prediction model, and a predetermined insulin injection amount prediction model; and outputting the determined insulin injection amount to administer to the target user without the target user wearing a continuous blood glucose monitoring device at each time of the plurality of times of the target user through the computer apparatus, wherein the determining the insulin injection amount at each time of the target user comprises:
inputting the characteristic information of the target user and the blood glucose content at the current time of the target user into the predetermined insulin injection amount prediction model to predict the insulin injection amount and determining the insulin injection amount at the current time;
inputting the insulin injection amount at the current time, the characteristic information of the target user, and the blood glucose content at the current time of the target user into the predetermined blood glucose prediction model to perform blood glucose prediction, and determining a blood glucose content of the target user at a next time corresponding to the current time; and
regarding the next time as a current time and returning to the inputting the characteristic information of the target user and the blood glucose content at the current time of the target user into the predetermined insulin injection amount prediction model to predict the insulin injection amount and determining the insulin injection amount at the current time; until the insulin injection amount at each time is determined, and obtaining the respective corresponding insulin injection amount at each time of the target user;

wherein the computer-executable instructions, when executed by one or more processors, cause the one or more processors to perform:
obtaining a marked training set and a unmarked training set, the marked training set comprising the characteristic information, the blood glucose content of each first-sample user at each sampling time, and the insulin injection amount of each first-sample user at each sampling time; the unmarked training set comprising characteristic information and a blood glucose content of each second-sample user at each sampling time;
initializing and obtaining an initial insulin injection amount prediction model; and
training the initial insulin injection amount prediction model based on the marked training set and the unmarked training set and determining the predetermined insulin injection amount prediction model;

wherein the initial insulin injection amount prediction model comprises first initial insulin injection amount prediction models;

wherein the determining the predetermined insulin injection amount prediction model comprises:
sampling the marked training set and determining mark training subsets, wherein the number of the mark training subsets is the same as the number of the first initial insulin injection amount prediction models, the mark training subset comprising the characteristic information, the blood glucose content at each sampling time, and the insulin injection amount at each sampling time of some sample users of the first-sample users;
training the corresponding first initial insulin injection amount prediction model based on the unmarked training set and the mark training subsets to obtain trained initial insulin injection amount prediction models;

performing weighted summation and averaging on each of the trained initial insulin injection amount prediction models based on weights, and obtaining an integrated insulin injection amount prediction model; and
determining the predetermined insulin injection amount prediction model according to the integrated insulin injection amount prediction model;

wherein the determining the predetermined insulin injection amount prediction model according to the integrated insulin injection amount prediction model comprises adjusting each of the weights in the integrated insulin injection amount prediction model based on the marked training set and determining the predetermined insulin injection amount prediction model; and wherein the determining the predetermined blood glucose prediction model comprises:
obtaining a sample marked training set; the sample marked training set comprising characteristic information, a blood glucose content at each sampling time, and an insulin injection amount at each sampling time of each third sample user;
initializing and obtaining an initial blood glucose prediction model; and
training the initial blood glucose prediction model based on the marked training set and determining the predetermined blood glucose prediction model.

4. A computer apparatus, comprising a memory and a processor, the memory stores computer-executable instructions that, when executed by the processor, causing the processor to perform a method comprising:
obtaining characteristic information and a blood glucose content at a current time of a target user through a computer apparatus, the characteristic information comprising clinical information and dietary information, wherein the clinical information comprises height, weight, fasting blood glucose content, and connecting peptide content;
determining an insulin injection amount at each time of a plurality of times after the current time of the target user through the computer apparatus and based on the characteristic information of the target user, the blood glucose content at the current time of the target user, a predetermined blood glucose prediction model, and a predetermined insulin injection amount prediction model; and
outputting the determined insulin injection amount to administer to the target user without the target user wearing a continuous blood glucose monitoring device at each time of the plurality of times of the target user through the computer apparatus, wherein the determining the insulin injection amount at each time of the target user comprises:
inputting the characteristic information of the target user and the blood glucose content at the current time of the target user into the predetermined insulin injection amount prediction model to predict the insulin injection amount and determining the insulin injection amount at the current time;
inputting the insulin injection amount at the current time, the characteristic information of the target user, and the blood glucose content at the current time of the target user into the predetermined blood glucose prediction model to perform blood glucose prediction, and determining a blood glucose content of the target user at a next time corresponding to the current time; and regarding the next time as a current time and returning to the inputting the characteristic information of the target user and the blood glucose content at the current time of the target user into the predetermined insulin injection amount prediction model to predict the insulin injection amount and determining the insulin injection amount at the current time; until the insulin injection amount at each time is determined, and obtaining the respective corresponding insulin injection amount at each time of the target user;

wherein the computer-executable instructions, when executed by one or more processors, cause the one or more processors to perform:

obtaining a marked training set and a unmarked training set, the marked training set comprising the characteristic information, the blood glucose content of each first-sample user at each sampling time, and the insulin injection amount of each first-sample user at each sampling time; the unmarked training set comprising characteristic information and a blood glucose content of each second-sample user at each sampling time;

initializing and obtaining an initial insulin injection amount prediction model; and training the initial insulin injection amount prediction model based on the marked training set and the unmarked training set and determining the predetermined insulin injection amount prediction model;

wherein the initial insulin injection amount prediction model comprises first initial insulin injection amount prediction models;

wherein the determining the predetermined insulin injection amount prediction model comprises:

sampling the marked training set and determining mark training subsets, wherein the number of the mark training subsets is the same as the number of the first initial insulin injection amount prediction models, the mark training subset comprising the characteristic information, the blood glucose content at each sampling time, and the insulin injection amount at each sampling time of some sample users of the first-sample users;

training the corresponding first initial insulin injection amount prediction model based on the unmarked training set and the mark training subsets to obtain trained initial insulin injection amount prediction models;

performing weighted summation and averaging on each of the trained initial insulin injection amount prediction models based on weights, and obtaining an integrated insulin injection amount prediction model; and determining the predetermined insulin injection amount prediction model according to the integrated insulin injection amount prediction model;

wherein the determining the predetermined insulin injection amount prediction model according to the integrated insulin injection amount prediction model comprises adjusting each of the weights in the integrated insulin injection amount prediction model based on the marked training set and determining the predetermined insulin injection amount prediction model; and wherein the determining the predetermined blood glucose prediction model comprises:

obtaining a sample marked training set; the sample marked training set comprising characteristic information, a blood glucose content at each sampling time, and an insulin injection amount at each sampling time of each third sample user;

initializing and obtaining an initial blood glucose prediction model; and training the initial blood glucose prediction model based on the marked training set and determining the predetermined blood glucose prediction model.

* * * * *